United States Patent
Maegerlein et al.

(10) Patent No.: US 7,544,819 B2
(45) Date of Patent: Jun. 9, 2009

(54) PROCESS FOR THE ASYMMETRIC EPOXIDATION OF OLEFINS

(75) Inventors: Wolfgang Maegerlein, Köln (DE); Matthias Beller, Ostseebad Nienhagen (DE); Christian Döbler, Lichtenhagen-Dorf (DE); Man Kin Tse, Rostock (DE); Santosh Bhor, Rostock (DE); Markus Klawonn, Rostock (DE)

(73) Assignee: Lanxess Deutschland GmbH, Leverkusen (DE)

( * ) Notice: Subject to any disclaimer, the term of this patent is extended or adjusted under 35 U.S.C. 154(b) by 519 days.

(21) Appl. No.: 11/051,279

(22) Filed: Feb. 4, 2005

(65) Prior Publication Data

US 2005/0203303 A1 Sep. 15, 2005

(30) Foreign Application Priority Data

Feb. 5, 2004 (DE) .................. 10 2004 005 725
May 19, 2004 (DE) .................. 10 2004 024 709

(51) Int. Cl.
*C07D 301/12* (2006.01)
*C07D 301/19* (2006.01)

(52) U.S. Cl. ..................... 549/531; 549/529

(58) Field of Classification Search .............. 549/529, 549/531
See application file for complete search history.

(56) References Cited

U.S. PATENT DOCUMENTS 4,943,644 A 7/1990 Drago et al. ............... 549/533
5,969,166 A 10/1999 Scharbert et al. ........... 549/512

OTHER PUBLICATIONS

Chem. Commun., 1997, pp. 1863-1864; Hisao Nishiyama et al; "Novel ruthenium-pyridinedi-carboxylate complexes of terpyridine and chiral bis(oxazolinyl)pyridine: a new catalytic system for alkene epoxidation with [bis(acetoxy)iodo]benzene as an oxygen donor".

Green Chemistry Feb. 1999, 1, pp. 39-41; Robert M. Stoop and Antonio Mezzetti; "Asymmetric epoxidation of olefins".

Organometallics 2000, 19, pp. 4117-4126; Stoop, Bachmann, Valentini, and Mezzetti; "Ruthenium(II) Complexes with Chiral Tetradentate $P_2N_2$ Ligands Catalyze the Asymmetric Epoxidation of Olefins with $H_2O_2$".

Journal of Molecular Catalysis, A: Chemical 1997, 124, pp. 91-97; Kureshy et al; "Chiral Ru(III) Metal complex-catalyzed aerobic enantioselective epoxidation of styrene derivatives with co-oxidation of aldehyde".

Qian C et al: "Asymmetric glyoxylate-ene reaction catalyzed by C2-symmetric chiral bis(oxazoline)-lanthanide complexes" Tetrahedron: Asymmetry, Elsevier Science Publishers, Amsterdam, NL, Bd. 11, Nr. 11, Jun. 2000, Seiten 2347-2357, XP004205796 ISSN: 0957-4166 Verbindung 1E.

Desimoni G et al: "The stereodivergent synthesis of chiral 4,5-disubstituted pybox ligands" 13, Nr. 15, Aug. 14, 2002, Seiten 1651-1654, XP004385891 ISSN: 0957-4166 Verbindungen 1A, 1B, 2A, 2B.

Li X et al: "The enantioselective diethylzinc addition to imines catalyzed by chiral Cu(II)-oxazoline complexes" Tetrahedron: Asymmetry, Elsevier Science Publishers, Amsterdam, NL. Bd. 14, Nr. 24, Dec. 12, 2003, Seiten 3819-3821, XP004476250 ISSN: 0957-4166 Verbindungen 4,5.

Brunner H et al: "Asymmetric catalysis. Part 153: Metal-catalysed enantioselective alpha-ketol rearrangement" Tetrahedron: Asymmetry, Elsevier Science Publishers, Amsterdam, NL, Bd. 14, Nr. 15, Aug. 1, 2003, Seiten 2177-2187, XP004441352 ISSN: 0957-4166 Verbindung 9H.

Lawrence N J et al: "An efficient protocol for the reduction f ketones with tin(II) complexes and PMHS" Tetrahedron Letters, Elsevier Science Publishers, Amsterdam, NL, Bd. 41, nr. 22, Jun. 2000, Seiten 4507-4512, XP004205598 ISSN: 0040-4039 Verbindungen 5D, 5E.

Dattagupta A et al: "Catalytic Enantioselective Allylic Oxidation of Olefins with Copper Complexes of Chiral Nonracemic Bis(oxazolinyl)pyridine Type Ligands" Tetrahedron Letters, Elsevier Science Publishers, Amsterdam, NL, Bd. 37, Nr. 15, Apr. 8, 1996, Seiten 2633-2636, XP004029756 ISSN: 0040-4039 Verbindung 2.

Desimoni G et al: "A new and highly efficient catalyst for the enantioselective Mukaiyama-Michael reaction between (E)-3-crotonoyl-1,3-oxazolidin-2- one and 2-trimethylsilyloxyfuran" Tetrahedron, Elsevier Science Publishers, Amsterdam, NL, Bd. 57, Nr. 51, Dec. 17, 2001, Seiten 10203-10212, XP004329195 ISSN: 0040-4020 Verbindungen 7A, 7B.

Gupta AD et al: "synthesis of homochiral bis(oxazolinyl)pyridine type ligands for asymmetric cyclopropanation reactions" Tetrahedron, Bd. 50, Nr. 48, 1994, Seiten 13725-13730, XP002331842 Verbindungen 4A, 4B.

Wei C et al: "enantioselective direct-addition of terminal alkynes to imines catalyzed by copper (I)pybox complex in water and toluene" J. Am. Chem. Soc., Bd. 124, 2002, Seiten 5638-5639, XP002331843 Verbindung 4.

Müller P et al: "carbenoid pathways in copper-catalyzed intramolecular cyclopropanations of phenyliodonium ylides" Helvetica Chimica Acta, Bd. 84, 2001, Seiten 1093-1111, XP002331844 Verbindungen XIV, XV.

Sekar G et al: "asymmetric kharasch reaction: catalytic enantioselective allylic oxidation of olefins using chiral pyridine bis(diphenyloxazoline)-copper complexes and tert. -butyl perbenzoate" Journal of Organic Chemistry, Bd. 63, 1998, Seiten 2961-2967, XP002331845 Verbindungen 4A-4D.

Slee DH et al: "development of potent non-carbohydrate imidazole-based small moleclule slectin inhibitors with anti-inflammatory activity" Journal of Medicinal Chemistry, Bd. 44, 2001, Seiten 2094-2107, XP002331846 Schema 1.

(Continued)

*Primary Examiner*—Bernard Dentz
(74) *Attorney, Agent, or Firm*—Michael A. Miller

(57) ABSTRACT

The present invention relates to a catalyst based on ruthenium complexes and to a process for the asymmetric epoxidation of olefins using catalysts based on ruthenium complexes.

6 Claims, No Drawings

OTHER PUBLICATIONS

Tse M K et al: "An improved protocol for the ruthenium(pybox)-catalyzed asymmetric alkene epoxidation" Tetrahedron Letters, Elsevier Science Publishers, Amsterdam, NL, Bd. 44, Nr. 40, Sep. 29, 2003, Seiten 7479-7483, XP004453451 ISSN: 0040-4039 Schema 1 Abbildung 1.

Miyabe H et al: "utility of the iridium complex of the pybox ligand in regio and enantioselective allylic substitution" Organic Letters, Bd. 6, Nr. 24, 2004, Seiten 4631-4634, XP002331857 Verbindung 9.

Desimoni G et al: "synergistic effect of pybox substituents and lanthanide cations in reversing the asymmetric induction in the catalysed Diels-Alder reaction between 3-acryloyl-1,3-oxazolidin-2-one and yclopentadiene" Eur. J. Org. Chem, 2004, Seiten 3057-3062, XP002331858 Verbindungen 5, 6, 8, 9.

Jun L et al: "highly enantioselective allylation of aldehydes catalyzed by indium(III)-pybox complex" Organic Letters, Bd. 7, Nr. 1, 2005, Seiten 159-161, XP002331859 Verbindungen 5, 6.

PROCESS FOR THE ASYMMETRIC EPOXIDATION OF OLEFINS

FIELD OF THE INVENTION

The present invention relates to a catalyst based on ruthenium complexes and to a process for the asymmetric epoxidation of olefins using catalysts based on ruthenium complexes.

BACKGROUND OF THE INVENTION

Olefins are readily available and inexpensive raw materials for industrial applications. They can be converted by oxidation into epoxides which are in turn of great importance as versatile intermediates in the synthesis of active compounds and fine chemicals (cosmetics industry, polymer industry, etc). Chiral epoxides are particularly valuable since they make it possible to obtain numerous structural elements, e.g. chiral diols or chiral amino alcohols, which frequently occur, in particular, in natural products and biologically active compounds. The most efficient and most economical method of synthesizing chiral epoxides is the catalytic, asymmetric epoxidation of olefins.

Mezetti et al. (Green Chemistry 1999, 1, 39-41; *Organometallics* 2000, 19, 4117-4126) discloses that olefins can be epoxidized in the presence of ruthenium catalysts and using hydrogen peroxide as oxidant, but the enantioselectivities of at most 42% are unsatisfactory and the yields are in most cases too low for industrial applications.

Other ruthenium-based systems, e.g. chiral Schiff-base complexes (Kureshi et al., *J. Mol. Catal. A: Chemical* 1997, 124, 91-97) are likewise quite inefficient in terms of yield and stereoselectivity.

A further process has been described by Nishiyama et al. (*Chem. Commun.* 1997, 1863-1864). In the epoxidation of trans-stilbene, enantioselectivities of 74% at yields of up to 63% were achieved using ruthenium-pyridine-2,6-dicarboxylate complexes having chiral bis(oxazolinyl)pyridine ligands. However, a disadvantage of this process is that bis(acetoxy)iodobenzene has to be used as reoxidant. This reagent is unattractive for industrial processes because of its high price.

There is therefore still a need to develop a general and efficient process for the asymmetric epoxidation of olefins, which displays high chemoselectivities and enantioselectivities and also gives good product yields. At the same time, the use of a both inexpensive and environmentally friendly oxidant is desirable from an industrial point of view.

SUMMARY OF THE INVENTION

We have now found a process for preparing stereoisomerically enriched compounds of the formula (I),

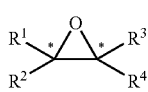

(I)

where

"*" is a carbon atom having an (R) or (S) configuration and $R^1$, $R^2$, $R^3$ and $R^4$ are each, independently of one another, hydrogen, alkyl, aryl, arylalkyl, haloalkyl or a radical of one of formulae (IIa) to (IIf)

A-B-D-E (IIa)

A-E (IIb)

A-SO$_2$-E (IIc)

A-B—SO$_2$R$^6$ (IId)

A-SO$_3$W (IIe)

A-COW (IIf)

where, in the formulae (IIa) to (IIf)

A is absent or is an alkylene or haloalkylene radical and

B is absent or is oxygen or NR$^5$, where

R$^5$ is nitrogen, arylalkyl or aryl, and

D is a carbonyl group and

E is R$^6$, OR$^6$, NHR$^7$ or N(R$^7$)$_2$, where

R$^6$ is alkyl, arylalkyl or aryl and the radicals R$^7$ are each, independently of one another, alkyl, arylalkyl or aryl or the moiety N(R$^7$)$_2$ is a cyclic amino radical having from 4 to 12 carbon atoms and W is OH, NH$_2$, or OM, where M is an alkali metal ion, half an equivalent of an alkaline earth metal ion, an ammonium ion or an organic ammonium ion, or two of the radicals $R^1$, $R^2$, $R^3$ and $R^4$ are together part of a 3- to 7-membered ring having a total of from 3 to 16 carbon atoms, which is characterized in that compounds of the formula (III),

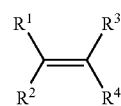

(III)

where $R^1$, $R^2$, $R^3$ and $R^4$ are each, independently of one another, as defined above, are reacted with compounds of the formula (IV),

R$^8$—OOH (IV)

where R$^8$ is hydrogen, alkyl or arylalkyl, with the reaction being carried out in the presence of a ruthenium complex which bears as ligands both compounds of the formula (V)

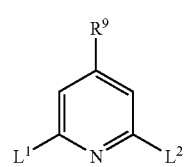

(V)

where R$^9$ is hydrogen, halogen, hydroxy, hydroxycarbonyl, alkoxycarbonyl, alkoxy, alkyl, arylalkyl or aryl and $L^1$ and $L^2$ are each, independently of one another, a radical of the formula (VI-a) or a radical of the formula (VI-b), but are preferably identical radicals of the formula (VI-a) or of the formula (VI-b)

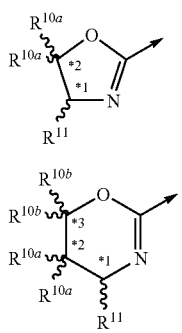

where "*1" and/or "*2" and/or "*3" are each an asymmetric carbon atom in the (R) or (S) configuration, with preference being given to "*1" being an asymmetric carbon atom in the (R) or (S) configuration and "*2" and/or "*3" likewise being able to be such a carbon atom, the arrow points to the point of bonding to the central pyridine ring and $R^{10a}$, $R^{10b}$ and $R^{11}$ are each, independently of one another, alkyl, alkoxyalkyl, trialkylsiloxyalkyl, alkoxycarbonyl, arylalkyl or aryl or $R^{10a}$ and $R^{11}$ or $R^{10a}$ and $R^{10b}$ are part of a cyclic radical having a total of from 5 to 16 carbon atoms and $R^{11}$ and/or in each case one or both radicals $R^{10a}$ and/or $R^{10b}$, preferably in each case one or both radicals $R^{10a}$ and/or $R^{10b}$, may also be hydrogen,
and compounds of the formula (VII)

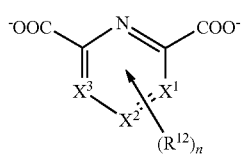

where
$X^1$, $X^2$ and $X^3$ are each, independently of one another, N, CH or $CR^{12}$ and
$R^{12}$ is hydrogen, halogen, hydroxy, hydroxycarbonyl, alkoxycarbonyl, alkoxy, alkoxyalkyl, arylalkyl or aryl and n is 0, 1, 2 or 3, preferably 0 or 1 and more preferably 0.

DETAILED DESCRIPTION OF THE INVENTION

For the purposes of the invention, stereoisomerically enriched means that one diastereomer or enantiomer is present in a higher relative proportion than the other diastereomers or the other enantiomer.

The present invention encompasses all definitions of radicals, parameters and explanations above and below, in general terms or in preferred ranges, in any combination with one another, i.e. also between the respective ranges and preferred ranges.

For the purposes of the present invention, aryl preferably refers, unless indicated individually, to carbocyclic aromatic radicals having from 6 to 24 skeletal carbon atoms or heteroaromatic radicals having from 5 to 24 skeletal carbon atoms in which no, one, two or three skeletal carbon atoms per ring, but at least one skeletal carbon atom in the total molecule, can be replaced by heteroatoms selected from the group consisting of nitrogen, sulphur and oxygen. Furthermore, the carbocyclic aromatic radicals or heteroaromatic radicals can be substituted by up to five identical or different substituents per ring selected from the group consisting of hydroxy, fluorine, nitro, cyano, free or protected formyl, $C_1$-$C_{12}$-alkyl, $C_5$-$C_{14}$-aryl, $C_6$-$C_{15}$-arylalkyl, —PO-[($C_1$-$C_8$)-alkyl]$_2$, —PO-[($C_5$-$C_{14}$)-aryl]$_2$, —PO-[($C_1$-$C_8$)-alkyl)($C_5$-$C_{14}$)-aryl)], tri($C_1$-$C_8$-alkyl)siloxyl or radicals of the formulae (IIa) to (IIf). The same applies to the aryl part of an arylalkyl radical.

For example, aryl is preferably phenyl, naphthyl or anthracenyl which may be substituted by one, two or three radicals selected independently from the group consisting of $C_1$-$C_6$-alkyl, $C_5$-$C_{14}$-aryl, $C_1$-$C_6$-alkoxy, $C_1$-$C_6$-alkoxycarbonyl, halogen, hydroxy, nitro or cyano.

For the purposes of the present invention alkyl or alkylene or alkoxy is preferably, unless indicated individually, in each case independently, a straight-chain, cyclic, branched or unbranched alkyl or alkylene or alkoxy radical which may be further substituted by $C_1$-$C_4$-alkoxy radicals. The same applies to the alkylene part of an arylalkyl radical.

For example, alkyl is preferably methyl, ethyl, n-propyl, isopropyl, n-butyl, tert-butyl, n-pentyl, cyclohexyl and n-hexyl, n-heptyl, n-octyl, isooctyl, n-decyl and n-dodecyl.

For example, alkylene is preferably methylene, 1,1-ethylene, 1,2-ethylene, 1,1-propylene, 1,2-propylene, 1,3-propylene, 1,1-butylene, 1,2-butylene, 2,3-butylene and 1,4-butylene, 1,5-pentylene, 1,6-hexylene, 1,1-cyclohexylene, 1,4-cyclohexylene, 1,2-cyclohexylene and 1,8-octylene.

For example, alkoxy is preferably methoxy, ethoxy, isopropoxy, n-propoxy, n-butoxy, tert-butoxy and cyclohexyloxy.

For the purposes of the present invention, arylalkyl is preferably, unless indicated individually, in each case independently, a straight-chain, cyclic, branched or unbranched alkyl radical which may be monosubstituted or polysubstituted, more preferably monosubstituted, by aryl radicals as defined above.

For the purposes of the present invention, haloalkyl or haloalkylene is preferably, unless indicated individually, in each case independently, a straight-chain, cyclic, branched or unbranched alkyl radical which may be monohalogenated, polyhalogenated or perhalogenated by halogen atoms selected independently from the group consisting of fluorine, chlorine, bromine and iodide.

For example, $C_1$-$C_8$-haloalkyl is preferably trifluoromethyl, trichloromethyl, 2,2,2-trifluoroethyl, pentafluoroethyl and nonafluorobutyl; $C_1$-$C_8$-fluoroalkyl is trifluoromethyl, 2,2,2-trifluoroethyl, pentafluoroethyl and nonafluorobutyl.

Protected formyl is a formyl radical which is protected by conversion into an aminal, acetal or a mixed aminal-acetal, with the aminals, acetals and mixed aminal-acetals being able to be acyclic or cyclic.

Preferred compounds of the formulae (I), (IV), (V) and (VII) are defined below.

In the formula (I), $R^1$, $R^2$, $R^3$ and $R^4$ are each preferably, independently of one another, hydrogen, $C_1$-$C_8$-alkyl, $C_5$-$C_{14}$-aryl, $C_6$-$C_{15}$-arylalkyl, $C_1$-$C_8$-haloalkyl or two of the radicals $R^1$, $R^2$, $R^3$ and $R^4$ are together part of a 3- to 7-membered ring having a total of from 3 to 16 carbon atoms.

More preference is given to compounds in which at least one, even more preferably at least two, radicals $R^1$, $R^2$, $R^3$ and $R^4$ are hydrogen.

In the formula (IV), $R^8$ is preferably hydrogen or $C_3$-$C_6$-alkyl, more preferably hydrogen or tert-butyl and most preferably hydrogen.

In the formula (V), $R^9$ is preferably hydrogen, halogen, $C_1$-$C_4$-alkoxy, $C_1$-$C_4$-alkyl, phenyl, more preferably hydrogen or phenyl.

Furthermore, $L^1$ and $L^2$ in the formula (V) are identical radicals of the formula (VI-a) or (VI-b).

Preference is given to the radicals $R^{10a}$ and/or $R^{10b}$ each being, independently of one another, hydrogen, methyl or phenyl. Particular preference is given to in each case one of the radicals $R^{10a}$ and/or $R^{10b}$ being methyl or phenyl and the second radical $R^{10a}$ and/or $R^{10b}$ and, if applicable, the two other radicals $R^{10a}$ or $R^{10b}$ being hydrogen, or one radical $R^{10a}$ being hydrogen and the second radical $R^{10a}$ together with $R^{11}$ forming an indanediyl group. More preferably, $R^{10a}$ in the formula (VI-a) and $R^{10a}$ and $R^{10b}$ in the formula (VI-b) are each hydrogen.

The radical $R^{11}$ is preferably methyl, isopropyl, tert-butyl, 2-naphthyl, phenyl, 2-chlorophenyl, benzyl, hydroxymethyl, tributylsiloxymethyl, 2-tributylsiloxyethyl or methoxycarbonyl.

In compounds of the formula (VII), $R^{12}$ is preferably hydrogen, hydroxy, $C_1$-$C_4$-alkoxy or phenyl, more preferably hydrogen.

Preference is given to at least two, preferably three, of the radicals $X^1$, $X^2$, $X^3$ being CH or $CR^{12}$.

n is preferably 0 or 1 and more preferably denotes one substitutent in the 4 position.

Preferred ruthenium complexes are complexes of the formula (VIII)

[Ru(V)(VII)]                                              (VIII)

where (V) denotes a compound of the formula (V) and (VII) denotes a compound of the formula (VII). Such complexes can be prepared in a manner known per se by methods analogous to those described in the references cited at the outset.

Compounds of the formula (V) are, with the exception of compounds in which $L^1$ and $L^2$ are each a radical of the formula (VI-a), where the radicals $R^{10a}$ are each hydrogen and $R^{11}$ is isopropyl or phenyl, previously unknown and are therefore encompassed by the present invention. The same applies to the ruthenium complexes which are used in the process of the invention and are derived from such compounds of the formula (V), such as ruthenium complexes of the formula (VIII).

Examples of such compounds of the formula (V) are 4-Chloro-2,6-bis[4'-(S)-phenyloxazolin-2'-yl]pyridine, 4-phenyl-2,6-bis[4'-(S)-phenyloxazolin-2'-yl]pyridine, 2,6-bis[(R)-4'-(1''-naphthyl)-5',6'-dihydro4'H-[1',3']oxazin-2'-yl]pyridine and 2,6-bis[(R)-4'-(2''-naphthyl )-5',6'-dihydro-4'H-[1',3']oxazin-2'-yl]pyridine.

Compounds of the formula (V) can be prepared, for example, by the method of Nishiyama et al., *Organometallics* 1991, 10, 500-508.

Preferably, the process of the invention is carried out in the presence of organic solvents, in particular secondary or tertiary alcohols, aprotic polar solvents, ketones, chlorinated hydrocarbons and aromatic hydrocarbons. For the purposes of the present invention, aprotic polar solvents are solvents which have a dielectric constant at 25° C. of 5 or more and a $pK_a$ based on an aqueous reference scale at 25° C. of 20 or more. Particular preference is given to using secondary and tertiary alcohols, in particular t-amyl alcohol and t-butyl alcohol, in the process of the invention.

The reaction is, for example, carried out by placing the compounds of the formula (III) and the ruthenium complex and, if appropriate, an additive together with an organic solvent in a reaction vessel and adding the oxidant, if appropriate as a solution in a suitable organic solvent. In a preferred embodiment, a solution of the oxidant is metered into the reaction mixture over a period of from 10 minutes to 24 hours.

The reaction time (further stirring time) can be, for example, up to 24 hours, preferably up to 5 hours and preferably up to 2 hours.

The reaction can be carried out at temperatures of from −20° C. to 150° C., preferably from 0 to 80° C., more preferably from 0° C. to 40° C., and most preferably from 15° C. to 30° C.

The pressure in the reaction is not critical and can be, for example, from 0.5 to 100 bar, preferably from 0.8 to 10 bar. More preference is given to ambient pressure.

As compounds of the formula (IV), preference is given to using tert-butyl hydroperoxide or hydrogen peroxide in the process of the invention. The oxidant is preferably used in an amount of from 1 to 10 molar equivalents based on compounds of the formula (III), more preferably from 1 to 5 molar equivalents and most preferably from 1 to 3 molar equivalents. It may be advantageous to use the oxidant as a solution in a solvent, preferably as a solution in water.

According to the process of the present invention, additives can be added to the reaction mixture. Examples of suitable additives include: amines, phosphites, phosphine oxides, N-methylmorpholine N-oxide, 2,2,6,6-tetramethylpiperidin-1-yl oxide, pyridines, pyridine N-oxide, imidazoles, quinoline, quinoline N-oxide, 2,2'-bipyridyl, 2,2'-bipyridyl N,N'-dioxide, ammonium salts, aromatic and aliphatic carboxylic acids, carboxylic anhydrides, (R)- or (S)-alkanesulfinamides and aromatic alcohols. These additives are preferably used in an amount of from 5 to 100 mol % based on compounds of the formula (III), more preferably from 10 to 50 mol % and very most preferably 20 mol %.

For the purposes of the present invention, the ruthenium complex can either be used as an isolated complex or be generated in situ in the reaction mixture. In the latter case, a suitable ruthenium precursor complex, e.g. [Ru(p-cymene)$Cl_2$]$_2$, and the two ligands of the formulae (V) and (VII) are combined in the reaction mixture.

Isolated complexes are, for example,
[Ru(4-chloro-2,6-bis[4'-(S)-phenyloxazolin-2'-yl]pyridine) (pyridine-2,6-dicarboxylate)]
[Ru(4-phenyl-2,6-bis[4'-(S)-phenyloxazolin-2'-yl]pyridine) (pyridine-2,6-dicarboxylate)]
[Ru(2,6-bis[4'-(S)-isopropyloxazoline-2'-yl]pyridine)(pyridine-2,6-dicarboxylate)]
[Ru(2,6-bis[(R)-4'-phenyl-5',6'-dihydro-4'H-[1',3']oxazin-2'-yl]pyridine)(pyridine-2,6-dicarboxylate)]
[Ru(2,6-bis[(R)-4'-(1''-naphthyl)-5',6'-dihydro-4'H-[1',3'] oxazin-2'-yl]pyridine)(pyridine-2,6-dicarboxylate)]
[Ru(2,6-bis[(R)-4'-(2''-naphthyl)-5',6'-dihydro-4'H-[1',3'] oxazin-2'-yl]pyridine)(pyridine-2,6-dicarboxylate)]

The preparation of the isolated complexes is preferably likewise carried out by combining a suitable ruthenium precursor complex such as [Ru(p-cymene)$Cl_2$]$_2$, and the two ligands of the formulae (V) and (VII) by, for example, introducing the ruthenium precursor complex with the ligand of the formula (V) into a suitable solvent in an inert gas atmosphere and adding a solution of the ligand of the formula (VII), subsequently heating the reaction mixture and isolating the ruthenium complex after work-up by means of extraction, drying and optionally subsequent chromatographic purification and/or recrystallization.

For the purposes of the present invention, the amount of ruthenium complex used or of ruthenium precursor complex used is, for example, in the range from 0.01 to 20 mol %, preferably from 1 to 10 mol % and more preferably from 2 to 5 mol %.

Compounds of the formula (I) can be obtained in good yields with high stereoisomeric or enantiomeric excesses in the manner prescribed by the invention. The work-up can be carried out in a known manner, e.g. by quenching with water, extraction with a suitable organic solvent and distillation or recrystallization of the epoxide.

The compounds of the formula (I) which can be prepared according to the invention are particularly useful for preparing pharmaceuticals, agrochemicals, polymers or intermediates for these.

In the process of the present invention, the asymmetric epoxidation of olefins proceeds with high chemoselectivity and enantioselectivity and gives very good product yields. At the same time, the ability to use the inexpensive oxidant hydrogen peroxide is a particular advantage.

EXAMPLES

General Method:

In a typical experiment, an olefin (0.5 mmol) and the ruthenium complex catalyst [Ru(S,S-2,6-bis[4'-(S)-phenyloxazolin-2'-yl]pyridine)(pyridine-2,6-dicarboxylate)] (0.025 mmol) were admixed with t-amyl alcohol (9 ml) and an additive was added if applicable. A solution of the oxidant (0.75 mmol) in t-amyl alcohol (1 ml) was metered into this mixture over a period of 12 hours. After the reaction was complete (monitoring of the conversion by GC-FID), the reaction mixture was quenched with saturated $Na_2SO_3$ solution (about 10 ml) and extracted twice with dichloromethane (10 ml each time). After removal of the solvent by distillation, the product was purified by column chromatography. All products described below were confirmed by GC-MS and NMR data and comparison with authentic samples (GC-FID).

Example 1

Use of trans-stilbene and $H_2O_2$ as oxidant in the general method gave trans-stilbene oxide in a yield of 99% and an ee of 67%.

Example 2

Use of trans-stilbene and $H_2O_2$ as oxidant in the presence of 0.025 mmol of 2,2'-bipyridyl N,N'-dioxide as additive in the general method gave stilbene oxide in a yield of 96% and an ee of 71%.

Example 3

Use of trans-stilbene and $H_2O_2$ as oxidant and the catalyst [Ru(4-chloro-2,6-bis[4'-(S)-phenyloxazolin-2'-yl]pyridine) (pyridine-2,6-dicarboxylate)] in the general method gave trans-stilbene oxide in a yield of 93% and an ee of 71%.

Example 4

Use of trans-stilbene and $H_2O_2$ as oxidant and the catalyst [Ru(4-phenyl-2,6-bis[4'-(S)-phenyloxazolin-2'-yl]pyridine) (pyridine-2,6-dicarboxylate)] (0.025 mmol) in the general method gave trans-stilbene oxide in a yield of 97% and an ee of 69%.

Example 5

Use of trans-stilbene and $H_2O_2$ as oxidant and the catalyst [Ru(2,6-bis[4'-(S)-isopropyloxazolin-2'-yl]pyridine)(pyridine-2,6-dicarboxylate)] (0.025 mmol) in the general method gave trans-stilbene oxide in a yield of 100% and an ee of 54%.

Example 6

Use of styrene and $H_2O_2$ as oxidant in a procedure analogous to Example 1 gave styrene oxide in a yield of 71% and an ee of 31%.

Example 7

Use of styrene and $H_2O_2$ as oxidant and acetic acid in a procedure analogous to Example 1 gave styrene oxide in a yield of 75% and an ee of 42%.

Example 8

Use of p-chlorostyrene and t-BuOOH as oxidant in a procedure analogous to Example 1 gave p-chlorostyrene oxide in a yield of 48% and an ee of 34%.

Example 9

Use of p-fluorostyrene and t-BuOOH as oxidant in a procedure analogous to Example 1 gave p-fluorostyrene oxide in a yield of 54% and an ee of 34%.

Example 10

Use of α-methylstyrene and $H_2O_2$ as oxidant in a procedure analogous to Example 1 gave α-methylstyrene oxide in a yield of 52% and an ee of 13%.

Example 11

Use of β-methylstyrol and $H_2O_2$ as oxidant in a procedure analogous to Example 1 gave β-methylstyrene oxide in a yield of 82% and an ee of 58%.

Example 12

Use of 2-methyl-1-phenyl-1-propene and t-BuOOH as oxidant in a procedure analogous to Example 1 gave 2-methyl-1-phenyl-1-propene oxide in a yield of 95% and an ee of 65%.

Example 13

Use of 1,2-diphenyl-1-propene and t-BuOOH as oxidant in the general method gave 1,2-diphenyl-1-propene oxide in a yield of 93% and an ee of 22%.

Example 14

Use of triphenylethylene and t-BuOOH as oxidant in a procedure analogous to Example 1 gave triphenylethylene oxide in a yield of 90% and an ee of 8%.

Example 15

Use of 1-phenylcyclohexene and $H_2O_2$ as oxidant in a procedure analogous to Example 1 gave 1-phenylcyclohexene oxide in a yield of 87% and an ee of 12%.

Example 16

Use of trans-stilbene and $H_2O_2$ as oxidant in a procedure analogous to Example 1, but with generation of the catalyst in situ from 0.0125 mol of [Ru(p-cymene)$Cl_2$]$_2$, 0.025 mol of 2,6-bis[4'-(S)-phenyloxazolin-2'-yl]pyridine and 0.025 mol of disodium pyridine-2,6-dicarboxylate, gave trans-stilbene oxide in a yield of 96% and an ee of 61%.

TABLE 1

Tabular summary of Examples 1 to 16 of the asymmetric
epoxidation of olefins in the presence of ruthenium complexes

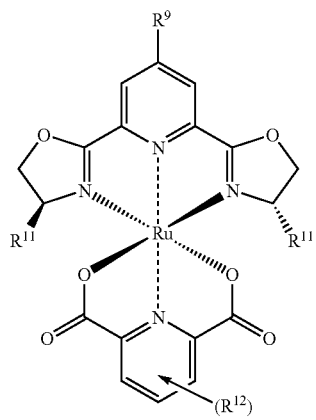

| Ex. | Olefin | Oxidant | Additive | Catalyst | Yield [%] | ee [%] |
|---|---|---|---|---|---|---|
| 1 | Ph-CH=CH-Ph | $H_2O_2$ | — | $R^{11}$ = Ph; $R^9$ = H; $R^{12}$ = H | 99 | 67 |
| 2 | Ph-CH=CH-Ph | $H_2O_2$ | 5 mol % of 2,2'-bipyridyl N,N'-oxide | $R^{11}$ = Ph; $R^9$ = H; $R^{12}$ = H | 96 | 71 |
| 3 | Ph-CH=CH-Ph | $H_2O_2$ | — | $R^{11}$ = Ph; $R^9$ = Cl; $R^{12}$ = H | 93 | 71 |
| 4 | Ph-CH=CH-Ph | $H_2O_2$ | — | $R^{11}$ = Ph; $R^9$ = Ph; $R^{12}$ = H | 97 | 69 |
| 5 | Ph-CH=CH-Ph | $H_2O_2$ | — | $R^{11}$ = i-Pr; $R^{12} = R^9$ = H | 100 | 54 |
| 6 | Ph-CH=CH$_2$ | $H_2O_2$ | — | $R^{11}$ = Ph; $R^{12} = R^9$ = H | 71 | 31 |
| 7 | Ph-CH=CH$_2$ | $H_2O_2$ | 20 mol% of acetic acid | $R^{11}$ = Ph; $R^9 = R^{12}$ = H | 75 | 42 |
| 8 | p-Cl—Ph-CH=CH$_2$ | t-BuOOH | — | $R^{11}$ = Ph; $R^{12} = R^9$ = H | 48 | 34 |
| 9 | p-F—Ph-CH=CH$_2$ | t-BuOOH | — | $R^{11}$ = Ph; $R^{12} = R^9$ = H | 54 | 34 |
| 10 | Ph-C(CH$_3$)=CH$_2$ | $H_2O_2$ | — | $R^{11}$ = Ph; $R^{12} = R^9$ = H | 52 | 13 |

TABLE 1-continued

Tabular summary of Examples 1 to 16 of the asymmetric
epoxidation of olefins in the presence of ruthenium complexes

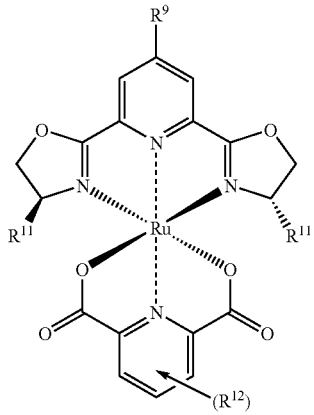

| Ex. | Olefin | Oxidant | Additive | Catalyst | Yield [%] | ee [%] |
|---|---|---|---|---|---|---|
| 11 | Ph-CH=CH-CH₃ | $H_2O_2$ | — | $R^{11}$ = Ph; $R^{12}$ = $R^9$ = H | 82 | 58 |
| 12 | Ph-C(CH₃)=CH₂ (β-methylstyrene) | t-BuOOH | — | $R^{11}$ = Ph; $R^{12}$ = $R^9$ = H | 95 | 65 |
| 13 | Ph-C(CH₃)=CH-Ph | t-BuOOH | — | $R^{11}$ = Ph; $R^{12}$ = $R^9$ = H | 93 | 22 |
| 14 | Ph-C(Ph)=CH-Ph | t-BuOOH | — | $R^{11}$ = Ph; $R^{12}$ = $R^9$ = H | 90 | 8 |
| 15 | 1-phenylcyclohexene | $H_2O_2$ | — | $R^{11}$ = Ph; $R^{12}$ = $R^9$ = H | 87 | 12 |
| 16 | Ph-CH=CH-Ph | $H_2O_2$ | — | $R^{11}$ = Ph $R^{12}$ = $R^9$ = H; in situ generation. | 96 | 61 |

Example 17

Use of styrene and H$_2$O$_2$ as oxidant and the catalyst [Ru(2,6-bis[(R)-4'-phenyl-5',6'-dihydro-4'H-[1',3']oxazin-2'-yl]pyridine)(pyridine-2,6-dicarboxylate)] (0.025 mmol) in the general method gave styrene oxide in a yield of 56% and an ee of 48%.

Example 18

Use of styrene and H$_2$O$_2$ as oxidant and the catalyst [Ru(2,6-bis[(R)-4'-(1''-napthyl)-5',6'-dihydro-4'H-[1',3']oxazin-2'-yl]pyridine)(pyridine-2,6-dicarboxylate)] (0.025 mmol) in the general method gave styrene oxide in a yield of 65% and an ee of 38%.

Example 19

Preparation of [Ru(2,6-bis[(R)-4'-(2''-naphthyl)-5',6'-dihydro-4'H-[1',3']oxazin-2'-yl]pyridine)(pyridine-2,6-dicarboxylate)]

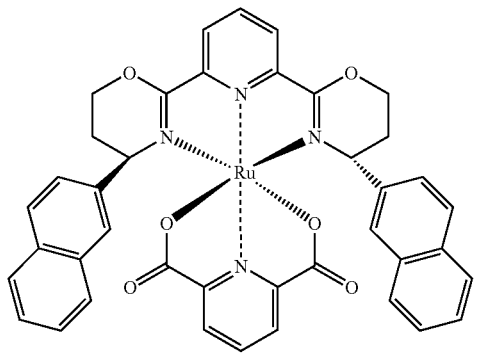

A solution of 64 mg of disodium pyridine-2,6-dicarboxylate (0.30 mmol) in 2 ml of a mixture of methanol/water (1:1) was added dropwise under an Ar atmosphere to a solution of 150 mg of 2,6-bis[(R)-4'-(2''-naphthyl)-5',6'-dihydro-4'H-[1',3']oxazin-2'-yl]pyridine (0.30 mmol) and 92 mg of [Ru(p-cymene)Cl$_2$]$_2$ (0.15 mmol) in 2 ml of methanol and the reaction mixture was heated at 65° C. for 1 hour. The reaction mixture was subsequently extracted with 30 ml of CH$_2$Cl$_2$, the organic phase was washed with 30 ml of water, dried over MgSO$_4$, filtered and the solvent was removed under reduced pressure. After subsequent chromatography over silica gel (70-230 mesh) using CH$_2$Cl$_2$/methanol (from 100:2 to 100:5) as gradated eluent and renewed removal of the solvent under reduced pressure, the product was recrystallized from CH$_2$Cl$_2$/n-hexane. This gave 138 mg of [Ru(2,6-bis[(R)-4'-(2''-naphthyl)-5',6'-dihydro-4'H-[1',3']oxazin-2'-yl]pyridine)(pyridine-2,6-dicarboxylate)] (60% of theory).

Example 20

Use of styrene and H$_2$O$_2$ as oxidant and the catalyst [Ru(2,6-bis[(R)-4'-(2''-naphthyl)-5',6'-dihydro-4'H-[1',3']oxazin-2'-yl]pyridine)(pyridine-2,6-dicarboxylate)] (0.025 mmol) in the general method gave styrene oxide in a yield of 59% and an ee of 48%.

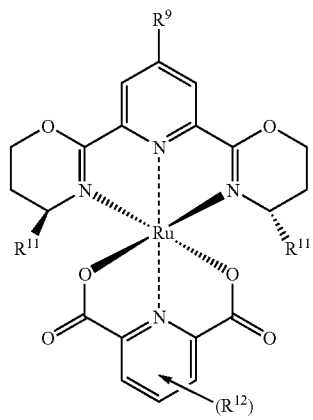

| Example | Olefin | Oxidant | Additive | Catalyst | Yield [%] | ee [%] |
|---|---|---|---|---|---|---|
| 17 | Ph⎯⎯ | H$_2$O$_2$ | — | R$^{11}$ = Ph; R$^9$ = H; R$^{12}$ = H | 56 | 48 |
| 18 | Ph⎯⎯ | H$_2$O$_2$ | — | R$^{11}$ = 1-naphthyl; R$^9$ = H; R$^{12}$ = H | 65 | 38 |
| 20 | Ph⎯⎯ | H$_2$O$_2$ | — | R$^{11}$ = 2-naphthyl; R$^9$ = H; R$^{12}$ = H | 59 | 48 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

The invention claimed is:

1. Process for preparing stereoisomerically enriched compounds of the formula (I),

wherein

"*" is a carbon atom having an (R) or (S) configuration and R$^1$, R$^2$, R$^3$ and R$^4$ are each, independently of one another, hydrogen, alkyl, aryl, arylalkyl, haloalkyl or a radical of one of formulae (IIa) to (IIf)

| A-B-D-E | (IIa) |
| A-E | (IIb) |
| A-SO$_2$-E | (IIc) |
| A-B—SO$_2$R$^6$ | (IId) |
| A-SO$_3$W | (IIe) |
| A-COW | (IIf) | wherein, in the formulae (IIa) to (IIf)
A is absent or is an alkylene or haloalkylene radical and
B is absent or is oxygen or NR$^5$, where $R^5$ is nitrogen, arylalkyl or aryl, and
D is a carbonyl group and
E is $R^6$, $OR^6$, $NHR^7$ or $N(R^7)_2$,
where
$R^6$ is alkyl, arylalkyl or aryl and
the radicals $R^7$ each, independently of one another, alkyl, arylalkyl or aryl or the moiety $N(R^7)_2$ is a cyclic amino radical having from 4 to 12 carbon atoms and
W is OH, $NH_2$, or OM, where M is an alkali metal ion, half an equivalent of an alkaline earth metal ion, an ammonium ion or an organic ammonium ion,
or two of the radicals $R^1$, $R^2$, $R^3$ and $R^4$ are together part of a 3- to 7-membered ring having a total of from 3 to 16 carbon atoms,
comprising reacting compounds of the formula (III),

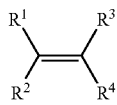
(III)

where $R^1$, $R^2$, $R^3$ and $R^4$ are each, independently of one another, as defined above,
with compounds of the formula (IV), $R^8$—OOH (IV)

where $R^8$ is hydrogen, alkyl or arylalkyl,
in the presence of a ruthenium complex which bears as ligands both compounds of the formula (V)

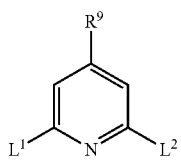
(V)

where $R^9$ is hydrogen, halogen, hydroxy, alkoxy, hydroxycarbonyl, alkoxycarbonyl, alkyl, arylalkyl or aryl and
$L^1$ and $L^2$ are each, independently of one another, a radical of the formula (VI-a) or a radical of the formula (VI-b)

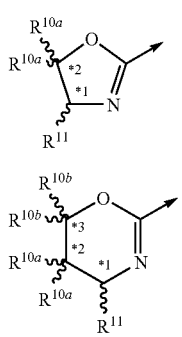
(VI-a)

(VI-b)

where "*1" and/or "*2" and/or "*3" are each an asymmetric carbon atom in the (R) or (S) configuration, the arrow points to the point of bonding to the central pyridine ring and $R^{10a}$, $R^{10b}$ and $R^{11}$ are each, independently of one another, alkyl, alkoxyalkyl, trialkylsiloxyalkyl, alkoxycarbonyl, arylalkyl or aryl or $R^{10a}$ and $R^{11}$ or $R^{10a}$ and $R^{10b}$ are part of a cyclic radical having a total of from 5 to 16 carbon atoms and $R^{11}$ and/or $R^{10a}$ and/or $R^{10b}$ may also be hydrogen, and compounds of the formula (VII)

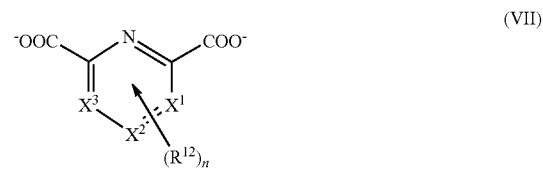
(VII)

where
$X^1$, $X^2$ and $X^3$ are each, independently of one another, N, CH or $CR^{12}$ and
$R^{12}$ is hydrogen, halogen, hydroxy, hydroxycarbonyl, alkoxycarbonyl, alkoxy, alkoxyalkyl, arylalkyl or aryl and
n is 0, 1, 2 or 3, preferably 0 or 1 and particularly preferably 0,
and wherein the reaction is carried out in the presence of secondary or tertiary alcohols as solvents.

2. Process according to claim 1, wherein $R^1$, $R^2$, $R^3$ and $R^4$ in the formula (I) are each independently of one another, hydrogen, $C_1$-$C_8$-alkyl, $C_5$-$C_{14}$-aryl, $C_6$-$C_{15}$-arylalkyl, $C_1$-$C_8$-haloalkyl or two of the radicals $R^1$, $R^2$, $R^3$ and $R^4$ are together part of a 3- to 7-membered ring having a total of from 3 to 16 carbon atoms.

3. Process according to claim 1, wherein $R^8$ n the formula (IV) is hydrogen or $C_3$-$C_6$-alkyl.

4. Process according to claim 1, wherein $R^8$ in the formula (IV) is hydrogen.

5. Process according to claim 1, characterized in that ruthenium complexes are complexes of the formula (VIII)

[Ru(V)(VII)] (VIII)

wherein (V) denotes a compound of the formula (V) and (VII) denotes a compound of the formula (VII), or complexes which are generated in situ in the reaction mixture from a suitable ruthenium precursor complex and the two ligands of the formulae (V) and (VII).

6. Process according to claim 1, further comprising adding an additive selected from the group consisting of amines, phosphites, phosphine oxides, N-methylmorpholine N-oxide, 2,2,6,6-tetramethylpiperidin-1-yl oxide, pyridines, pyridine N-oxide, imidazoles, quinoline, quinoline N-oxide, 2,2'-bipyridyl, 2,2'-bipyridyl N,N'-dioxide, ammonium salts, aromatic and aliphatic carboxylic acids, carboxylic anhydrides, (R)- or (S)-alkanesulfinamides and aromatic alcohols.

* * * * *